United States Patent
Brooks et al.

(10) Patent No.: US 11,464,466 B2
(45) Date of Patent: Oct. 11, 2022

(54) METHODS AND SYSTEMS FOR PERIODONTAL DISEASE SCREENING

(71) Applicant: NovoDynamics, Inc., Ann Arbor, MI (US)

(72) Inventors: Mark Brooks, Gregory, MI (US); David Ei, Whitmore Lake, MI (US); Sean McMillan, Ann Arbor, MI (US); David Rock, Saline, MI (US); Steven Schlosser, Gregory, MI (US)

(73) Assignee: NovoDynamics, Inc., Ann Arbor, MI (US)

( * ) Notice: Subject to any disclaimer, the term of this patent is extended or adjusted under 35 U.S.C. 154(b) by 713 days.

(21) Appl. No.: 16/506,732

(22) Filed: Jul. 9, 2019

(65) Prior Publication Data

US 2020/0015764 A1    Jan. 16, 2020

Related U.S. Application Data

(60) Provisional application No. 62/696,736, filed on Jul. 11, 2018.

(51) Int. Cl.
*G06T 7/00*      (2017.01)
*A61B 6/14*      (2006.01)
(Continued)

(52) U.S. Cl.
CPC ............ *A61B 6/145* (2013.01); *A61B 5/0088* (2013.01); *A61B 6/505* (2013.01); *A61C 9/0053* (2013.01);
(Continued)

(58) Field of Classification Search
CPC ....... A61B 6/145; A61B 5/0088; A61B 6/505; A61B 6/032; A61B 6/14; A61B 6/5217;
(Continued)

(56) References Cited

U.S. PATENT DOCUMENTS 6,651,060 B1    11/2003    Harper et al.
8,417,010 B1    4/2013    Colby
(Continued)

FOREIGN PATENT DOCUMENTS

CN    103347436 A    *    10/2013    ......... A61B 1/00009
CN    104507415 A    *    4/2015    ............ A61B 10/00
(Continued)

OTHER PUBLICATIONS

United States Patent and Trademark Office, International Search Report and Written Opinion for PCT/US2020/040930, dated Sep. 25, 2020, 7 pages.

*Primary Examiner* — Jose L Couso

(74) *Attorney, Agent, or Firm* — Cooley LLP

(57) ABSTRACT

Teeth are screened for periodontal disease using digitized images manipulated and annotated on a processor. A digitized radiographic image of a tooth shows locations of a bone boundary and a cemento-enamel junction (CEJ) of the tooth. The digitized radiographic image is marked on the processor with a location on the bone boundary and with a pair of CEJ points at opposite ends of the CEJ visible in the radiograph. A ratio between (a) a distance between the bone boundary location and the adjacent CEJ point as numerator and (b) a distance between the CEJ points as denominator is calculated on the processor and compared with a threshold ratio-value for a corresponding tooth from a database accessible by the processor. A calculated ratio-value which is greater than the database threshold ratio-value is indicative of periodontal disease in the tooth. The probability of the (Continued)

correct diagnostic decision is determined by the relative magnitude of the calculated ratio-value and the threshold ratio-value.

30 Claims, 10 Drawing Sheets

(51) Int. Cl.
    *A61B 6/00*     (2006.01)
    *A61C 9/00*     (2006.01)
    *A61B 5/00*     (2006.01)
    *A61B 6/03*     (2006.01)
    *A61C 19/04*     (2006.01)

(52) U.S. Cl.
    CPC .............. *A61B 6/032* (2013.01); *A61C 19/04* (2013.01); *G01N 2800/18* (2013.01); *G06T 2207/10116* (2013.01)

(58) Field of Classification Search
    CPC ......... A61B 6/461; A61B 6/467; A61B 6/463; A61B 6/469; A61B 5/4547; A61B 5/7267; A61B 6/5294; A61B 1/000096; A61B 5/0013; A61C 9/0053; A61C 19/04; A61C 7/002; A61C 13/0004; A61C 19/043; A61C 5/70; A61C 8/00; G01N 2800/18; G06T 2207/10116; G06T 2207/20081; G06T 2207/30036; G06T 2207/20084; G06T 7/0012; G06T 7/0014; G06T 2210/12; G06T 2210/41; G16H 50/30; G16H 30/40; G16H 50/20; G16H 30/20; G16H 10/60; G16H 50/70; G16H 40/63; G16H 40/67; G16H 20/00; G16H 50/50; G06V 10/82; G06V 2201/03; G06V 10/462; G06V 10/454; G06K 9/6271; G06K 9/6256; G06K 9/6259; G06K 9/6262; G06K 9/6269; G06K 9/627; G06K 9/6293; G06Q 30/0605; G06Q 50/26; G06Q 10/10; G06F 16/55; G06F 21/6245; G06F 21/6218; G06N 3/02; G06N 3/08–088; G06N 3/0454; G06N 20/00

See application file for complete search history.

(56) References Cited

U.S. PATENT DOCUMENTS

| | | |
|---|---|---|
| 9,463,081 B2 | 10/2016 | Urakabe |
| 9,710,599 B1 | 7/2017 | Johnson et al. |
| 9,940,677 B2 | 4/2018 | Brown |
| 10,285,635 B2 | 5/2019 | Motegi |
| 11,045,156 B2 | 6/2021 | Tsuji et al. |
| 2003/0112921 A1* | 6/2003 | Lang ............... A61B 6/583 378/54 |
| 2006/0285636 A1 | 12/2006 | Razzano |
| 2007/0047794 A1* | 3/2007 | Lang ............... A61B 6/583 382/132 |
| 2008/0033754 A1* | 2/2008 | Smith ............... G06Q 40/08 707/999.001 |
| 2009/0124882 A1* | 5/2009 | Massie ............... A61B 6/482 600/407 |
| 2010/0145734 A1 | 6/2010 | Becerra et al. |
| 2010/0185922 A1 | 7/2010 | Haas et al. |
| 2010/0210943 A1* | 8/2010 | Mahmoud ........... A61B 8/4245 600/437 |
| 2011/0036360 A1* | 2/2011 | Lang ............... G06T 7/0012 128/898 |
| 2012/0131034 A1 | 5/2012 | Kenedy et al. |
| 2013/0329854 A1 | 12/2013 | Spartiotis et al. |
| 2015/0130593 A1 | 5/2015 | Mats et al. |
| 2015/0213199 A1* | 7/2015 | Loeb ............... G06F 21/6245 705/3 |
| 2016/0151026 A1* | 6/2016 | Shibasaki ........... A61B 6/461 378/10 |
| 2016/0183866 A1* | 6/2016 | Tsuji ............... A61B 6/032 433/29 |
| 2017/0173262 A1 | 6/2017 | Veltz |
| 2018/0039733 A1 | 2/2018 | Golay |
| 2020/0100724 A1* | 4/2020 | Golay ............... G16H 70/60 |
| 2020/0146646 A1* | 5/2020 | Tuzoff ............... A61B 6/563 |
| 2021/0012426 A1 | 1/2021 | Brooks et al. |

FOREIGN PATENT DOCUMENTS

| | | | |
|---|---|---|---|
| JP | 5441141 B1 * | 3/2014 | ............. A61B 10/00 |
| WO | WO-2013018522 A1 * | 2/2013 | ............. A61B 6/032 |

\* cited by examiner

METHODS AND SYSTEMS FOR PERIODONTAL DISEASE SCREENING

CROSS-REFERENCE TO RELATED APPLICATION

This application claims the benefit of U.S. Provisional No. 62/696,736, filed Jul. 11, 2018, the entire content of which is incorporated herein by reference.

BACKGROUND OF THE INVENTION

1. Field of the Invention

The present invention relates generally to methods and systems for periodontal disease assessment. More particularly, the present invention relates to methods and systems for implementing and facilitating the evaluation of dental images and other patient information by experts and expert systems.

Centralized evaluations of periodontal disease are often problematic because available evidence submitted by practitioners can be ambiguous, requiring interpretation by expert periodontists. This can be a particular problem, for example, in insurance claim submissions where the ambiguity is sufficiently great that even skilled practitioners arrive at conflicting interpretations of the same data, thereby complicating final claim adjudication. Other instances where the inability to provide uniform, consistent periodontal evaluations can be problematic include the collection of population-based periodontal disease treatment data, peer group evaluations, and the like.

For these reasons, it would be desirable to provide improved methods and systems for periodontal disease assessment. In particular, it would be desirable to provide methods and systems for implementing and facilitating the evaluation of dental images and other patient information by experts and expert systems. Such methods and systems may find use in a variety of circumstances, including but not limited to periodontal insurance claim assessment, where evidence-based claim examination processes can be made more consistent, more accurate, less expensive and more reliable. At least some of these objectives will be met by the inventions described and claimed herein.

2. Description of the Background Art

U.S. Pat. No. 8,417,010, describes a method for diagnosis and evaluation of tooth decay and periodontal disease which includes image annotation.

SUMMARY OF THE INVENTION

The present invention provides a computer-assisted periodontal disease assessment tool that allows experts and expert systems to evaluate the presence and extent of periodontal disease in a patient based on a remotely generated, typically pre-standardized set of patient information including at least radiographic images of the patient dentition and typically also including other patient information. In some examples, these tools can provide periodontal insurers with a uniform, consistent, evidence-based decision-aid for insurance claims examination.

Exemplary decision-aid tools described herein typically incorporate a statistical model that relates quantitative radiographic measurements to allow claim evaluation based on whether existing bone loss meets the insurer's criteria for reimbursement of periodontitis treatment. Due to the tool's efficacy, the practical effect of relying on this decision-aid is to greatly reduce the subjective aspects of current claim examination practices, strengthen the evidence-based character of the review process and improve the consistency and accuracy of the claim examination process.

In a first aspect, the present invention provides a method performed on a processor for screening a tooth for periodontal disease. The method, for example, comprises providing a digitized radiographic image of a tooth, typically identified by a tooth number according to a tooth classification system, where the digitized radiographic image shows a bone boundary and a cemento-enamel junction (CEJ) of the tooth. The digitized radiographic image is loaded onto the processor and marked on the processor with a location on the bone boundary and with a pair of CEJ-endpoints at opposite ends of the CEJ visible in the radiograph. For example, a preferred location on the bone boundary may correspond to maximum bone loss relative to the adjacent tooth. A ratio is formed between (a) the distance between the bone boundary location and the adjacent CEJ-endpoint as numerator and (b) the distance between the CEJ-endpoints which represents a width of the tooth as denominator, and the ratio value for the tooth is calculated on the processor and compared with a threshold ratio-value for the corresponding tooth from a database accessible by the processor. A calculated ratio-value which is greater than the database threshold ratio-value is indicative of periodontal disease of the tooth. Moreover, on the basis of the relative magnitude of the calculated ratio and the database threshold value, the probability of periodontal disease of the tooth is calculated.

As used herein and in the claims, digitized information includes all forms of data that are in a form that can be presented by a processor on a display. In the case of radiographic images, the data sets will typically be in file-based, rasterized image formats such as JPEG, TIFF, PNG and BMP, although the data need not be held in file-format as is typically the case when a database is the source of the radiographic data. The image data sets will be in in a form that allows for quantitative analysis of the image by the processor, e.g. by counting of pixels to determine the relative distances between anatomical locations marked on the image by the processor, or can be converted to such a form.

In specific embodiments of this method, the location on the bone boundary is selected so that the line segment joining the adjacent CEJ-endpoint and the location accurately reflect the maximum bone loss adjacent to the tooth, and marking the digitized radiographic image comprises presenting the image on a monitor in communication with the processor and using an interface in communication with the processor to manually mark the location on the bone boundary and the locations of the CEJ-endpoints on the image. Alternatively, marking the digitized radiographic image may comprise automatically annotating the location on the bone boundary and the locations of the CEJ-endpoints on the image using an instruction set implemented by the processor. Such automated marking may be based on a machine-learning analysis of the results of manual marking of large numbers of patient images.

In further specific embodiments of this method, the processor may determine (a) the distance between the location on the bone boundary and the adjacent CEJ-endpoint and (b) the distance between the CEJ-endpoints by counting pixels on the digitized image. The radiographic image may be selected from the group consisting of a bitewing image, a periapical image, and a panoramic image in a standard digitized format. Often at least some of the digitized images may be further labeled with image identification information, including image type and semantic content.

In further specific embodiments of this method, the processor may determine (a) the distance between the location on the bone boundary and the adjacent CEJ-endpoint and (b) the distance between the CEJ-endpoints by counting pixels on the digitized image. The radiographic image may be selected from the group consisting of a bitewing image, a periapical image, and a panoramic image, where the digitized radiographic image is the result of digitizing a non-digital radiographic image (e.g., film). Often at least some of the digitized images may be further labeled with image identification information including image type and semantic content.

In further yet additional embodiments of the present invention, the methods may further comprise digitizing non-digital patient records other than images to produce digitized patient records, where at least some of these digitized records may be labeled with patient information. Exemplary non-image digitized records include at least some of patient dental probe-depth charts, patient correspondence, and dental photographs.

Images and other patient data may be provided in digitized form from submitted patient records. Alternatively, at least some of the submitted patient records may be in non-digital (analog) form, and the methods of the present invention may further comprise digitizing such non-digital radiographic images and/or other patient data prior to providing the digitized radiographic image and/or other patient information to the processor. The digitized images and other data may optionally be standardized before forwarding a patient claim to an expert.

As used in the claims and elsewhere herein, the term "standardized" means that the images will have a uniform orientation, scale, image contrast, brightness, sharpness and the like, which allow the expert and/or expert system to more accurately compare the data and annotate the images. In particular, the image standardization for the patient images will be selected to conform to the standardized images used for collecting data and determining threshold values as discussed elsewhere herein.

In still further embodiments of these methods, the database of threshold ratio-values has been generated by statistical analysis of the ratio between (a) a distance between the selected location on the bone boundary and the adjacent CEJ-endpoint as numerator and (b) the distance between CEJ-endpoints as denominator for a plurality of patients having pre-diagnosed tooth disease.

In still further embodiments of these methods, the database of threshold ratio-values has been generated by statistical analysis of the ratio between (a) a distance between the selected location on the bone boundary and the adjacent CEJ-endpoint as numerator and (b) the distance between the CEJ points as denominator for a plurality of patients having pre-diagnosed periodontal disease.

In a second aspect, the present invention provides a method for screening periodontal insurance claims. Such screening method comprise receiving periodontal insurance claims identifying at least one tooth as having periodontal disease, typically by tooth number according to a tooth classification system, and including patient identification information and radiographic images of each tooth identified as having periodontal disease. Each tooth identified as having periodontal disease in the insurance claim is evaluated by the methods described above, and those teeth found which do not meet the periodontal disease threshold with high probability, e.g. having a calculated ratio-value significantly less than the database threshold ratio-value, is optionally flagged for further evaluation by an expert.

The insurance claim evaluation methods may include any or all of the specific embodiments and features of the tooth screening methods described above. For example, the radiographic images will typically include bitewing, periapical, and/or panoramic images. The patient identification information will often include documents such as photographs, probe depth-charts, correspondence, and/or claim forms. The patient images and other information may be submitted in digital and/or non-digital formats, and the methods may comprise digitizing all non-digital patient information prior to making the digitized information part of the patient record. The digitized images and other data may optionally be standardized before forwarding a patient claim to an expert.

In a third aspect, the present invention provides a processor configured to perform the steps of any of the methods described previously and elsewhere herein. For example, the processor may be programmed or otherwise configured using hardware and software to receive a digitized radiographic image of a tooth, typically identified by a tooth number according to a tooth classification system, wherein the image shows a bone boundary and a cemento-enamel junction (CEJ) of the tooth. The digitized radiographic image is marked with a location on the bone boundary and a pair of CEJ-endpoints at opposite ends of the CEJ, and the processor calculates a ratio between (a) a distance between the bone boundary location and the adjacent CEJ-endpoint as numerator and (b) a distance between the CEJ-endpoints which represents a width of the tooth as denominator. The ratio-value for the tooth calculated on the processor is compared with a threshold ratio-value for a corresponding tooth from a database accessible by the processor, where a calculated ratio-value greater than the database threshold ratio value is indicative of periodontal disease in the tooth and the relative magnitude of the calculated ratio and the database threshold value determines the probability of periodontal disease of the tooth.

The processor may be further programmed or configured to implement any of the method steps described above or elsewhere herein. For example, the processor may be configured to allow a user to mark a location on the bone boundary and a location at the CEJ, where the location on the bone boundary is selected so that the line segment joining the adjacent CEJ-endpoint and the location accurately reflect the maximum bone loss adjacent to the tooth. Marking the digitized radiographic image may comprise presenting the image on a monitor in communication with the processor and using an interface in communication with the processor to manually mark the location on the bone boundary and the locations of the CEJ-endpoints on the image. Alternatively, the locations of the bone boundary and the CEJ-endpoints on the digitized radiographic image may be automatically annotated using an instruction set implemented by the processor.

The processor may be programmed to determine (a) the distance between the location on the bone boundary and the location of the CEJ points and (b) the distance between the CEJ points by counting pixels on the digitized image. The radiographic image may be selected from a group consisting of a bitewing image, a periapical image, or a panoramic image. Digitizing the image may include labeling each digitized image with image identification information, including image type and semantic content.

Non-digital records other than images may also be annotated with other patient information prior to producing digitized patient records. The digitized records may comprise at least some of patient probe-depth charts, patient correspondence, and patient photographs; digitizing a non-digital radiographic image may be performed prior to providing the digitized radiographic image, and the database of threshold ratio-values will typically have been generated by statistical analysis of the ratio between (a) a distance between the location on the bone boundary and adjacent CEJ-endpoint as numerator and (b) the distance between the CEJ-endpoints as denominator for a plurality of patients having pre-diagnosed periodontal disease.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
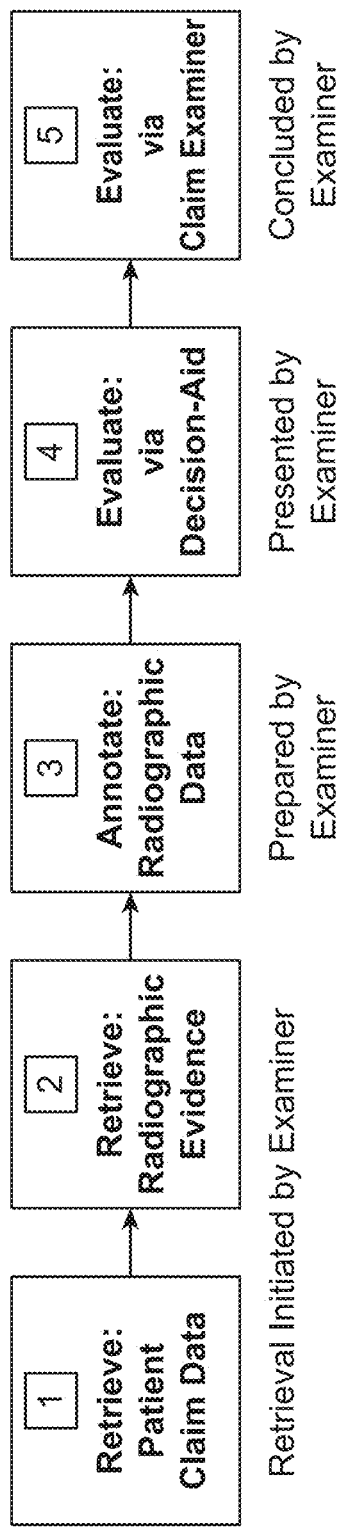
FIG. 1 is a chart illustrating the workflow in handling an insurance claim in accordance with the principles of the present invention.

Referring to FIG. 1, to evaluate a periodontitis treatment claim using a processor system in accordance with the principles of the present invention, a claim evaluator typically performs the following actions:

Step 1—Requests and displays patient claim data. A claim is ready for review when the summary claim forms and all supporting documentation have been submitted to the insurer. A claim examiner initiates a review by querying the claim database(s) to obtain the claim identifier, the dental provider's identifier, and the patient's identifying information as well as links to supporting documentation such as various types of radiographs, photographs, probe depth-charts and/or correspondence. The query results are displayed at the examiner's workstation in textual format.

Step 2—Requests and displays relevant radiographic evidence supporting the claim. The examiner queries the claim database(s) for relevant radiographic views such as bitewing, periapical or panoramic submitted by the dental provider. This data is presented at the examiner's workstation in image format for evaluation.

Step 3—Annotates the corresponding radiograph(s). Annotation of the radiographs is carried out using drawing tools designed for this purpose. The CEJ locations on each side of the tooth under consideration are marked as individual points (corresponding to a width at each end of the CEJ) and the line segment from each CEJ-endpoint to the neighboring bone boundary that shows the maximum extent of the estimated bone loss is drawn. The evaluation system records the geometric data generated by the annotation and converts it into linear metric information concerning CEJ endpoint separation and estimated bone loss. Steps 3-5 are applied to each tooth for which periodontitis-related bone loss is claimed.

Step 4—Inputs annotation data to periodontitis decision-aid and obtains advisory report. The metric data acquired in Step 3 is automatically entered into the periodontal decision-aid for evaluation. The decision-aid produces an advisory report concerning whether the bone loss found is sufficient to validate the presence of periodontal disease. A probability of correctness is returned for each tooth evaluated based on a previously established statistical model of periodontal disease.

Step 5—Accepts or denies the submitted claim and completes examination report. The claim examiner completes their report after evaluating all supporting information of the claim and that of the decision-aid's advisory report. Use of the advisory report is at the discretion of the reviewing periodontist.

The following discussion provides additional detail concerning the objectives and operation of the evaluation systems of the present invention while also identifying certain unique aspects.

Step 1: Retrieve and Display Patient Claim Data. Insurers collect claim-related data from providers through a variety of transfer mechanisms, including direct submission and submission via insurance claim clearinghouses. As a matter of transfer convenience, much of the claim data is delivered as images resulting from the scanning of various document types. The multiplicity of data transfer paths requires the insurers to support a variety of transfer protocols and file formats, some of which are tied to legacy data storage systems. This in turn, at least in the case of some insurers, has resulted in claim data being stored in one or more (typically non-interoperating) data systems in ways that often reduce claim examiner data retrieval processes to one of trial-and-error.

The evaluation system streamlines retrieval of claim materials by providing a unified, standardized interface for data retrieval that incorporates federated database retrieval when required by the insurer's existing information technology infrastructure. This integration of the insurer's claim systems is accomplished at the time of evaluation system installation through the use of configuration files that allow efficient customization of each installation.

Individual reimbursement claims typically involve the submission of one or more of the following document types stored in image format: radiographs, photographs, probe depth-charts and related correspondence. It is common for these image documents to be retained in the insurer's database(s) without any indication of document type, thereby slowing the search for a specific document supporting a claim—say, for instance, a radiograph.

The evaluation system incorporates proprietary document classification algorithms capable of automatically and accurately labeling each document type. This semantic labeling of document type allows claim materials to be searched efficiently and presented to the examiner in an organized and standardized manner.

There are two unique types of data organization enabled by the evaluation system: semantic labeling of the supporting documents of the claim; and standardization of the presentation of the claim data.

Semantic labeling of the scanned, image-formatted data is performed automatically through the use of appropriate algorithms. This allows individual documents to be tagged as a type of form (e.g., insurer-specific dental claim form), free-form text (e.g., correspondence), a radiograph, photograph or probe depth-chart. Further classification refinement also can be achieved where radiographs are tagged as bitewing, periapical, or panorama, photographs tagged as color, grey-scale or binary and forms tagged by specific layout identifiers (e.g., DD-Form 2017).

Figure 2:
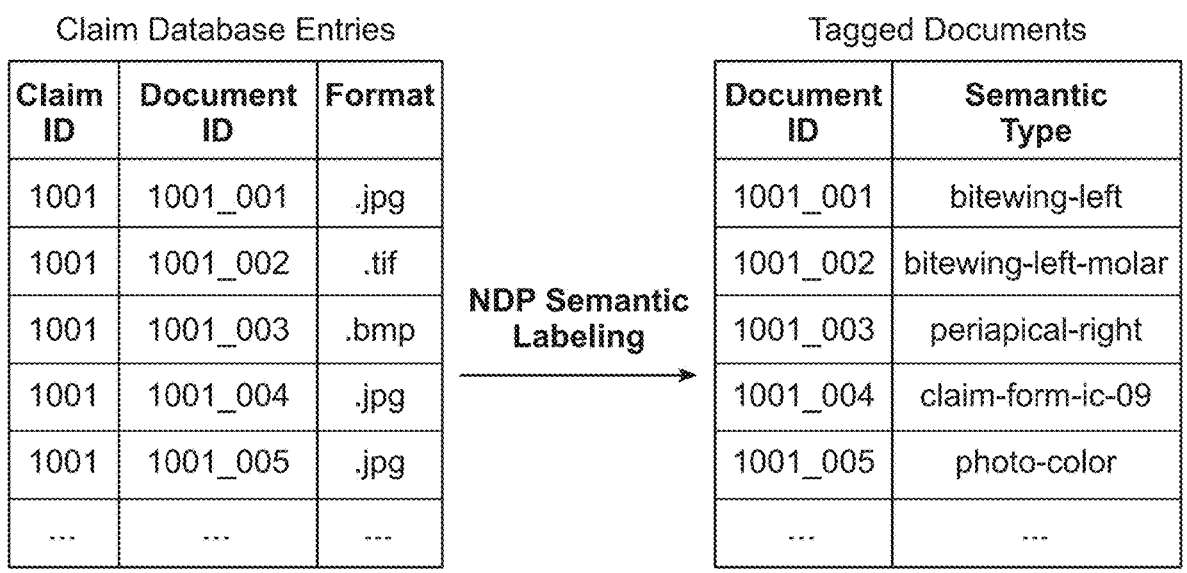
FIG. 2 is an example of semantic processing in accordance with the principles of the present invention.

Once the claim data is semantically-tagged, data queries can be precise, with specific data types obtained exclusively (e.g., bitewings), and presentation of the claim data organized so that it's possible to view, say, all submitted bitewings or all color photographs (and nothing else). Through semantic tagging, search and retrieval operations are made efficient by eliminating brute-force, trial-and-error queries. The semantic-tagging feature is exemplified in FIG. 2.

Step 2: Retrieve and Display Radiographic Evidence. Radiographic data submitted to insurers is prepared in a variety of ways, including computer screenshot, photocopy and direct digital readout. As a result, the radiographs are not of uniform image quality or orientation and are not normally optimized for human interpretation.

The evaluation system uses advanced image processing methods to standardize the presentation of radiographic data, enhance the images for interpretation by adjusting brightness and contrast and prepare them for human interpretation and annotation. To meet these goals, the system automatically extracts all relevant radiographic image data from the clinician-submitted image files, excluding superfluous elements, and labels each image element ("chip") according to its view-type, tooth-type, and location, using dental analysis software.

Figures 3, 4, 5, 6:
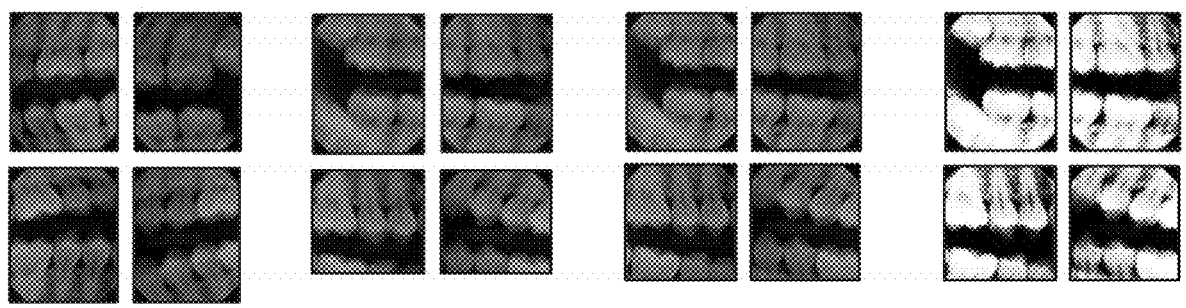
FIGS. 3-6 illustrate an exemplary set of radiographic images (bitewings) shown as they are being standardized for expert viewing in accordance with the principles of the present invention.

The process is partially exemplified in FIGS. 3-6, where the submitted input data (FIG. 3) has been photocopied with the radiographic sheet rotated and upside-down. The evaluation system automatically detects the misalignment and reorients the sheet (FIG. 4) before extracting the tooth data from the surrounding text and extraneous marks (FIG. 5) and performing image enhancement and, finally, establishing a standardized view (FIG. 6).

Figure 7:
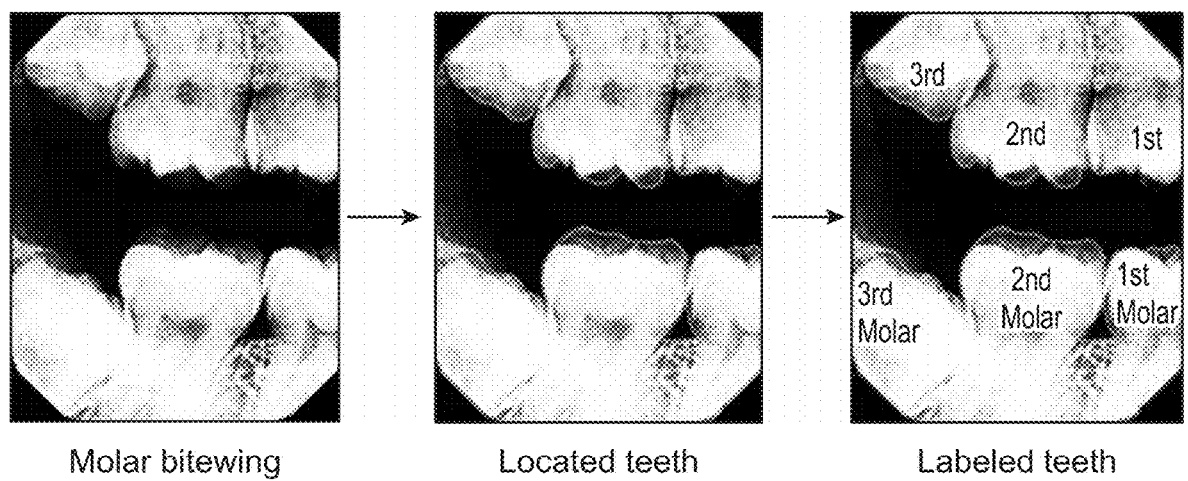
FIG. 7 illustrates automatic labelling of individual teeth (molars) in a standardized radiographic image in accordance with the principles of the present invention.

Additionally, in some cases it is desirable to locate and label individual teeth automatically. The evaluation system can be programmed and configured to perform these operations, as shown in FIG. 7.

Step 3: Annotate Radiographic Data. Radiographs submitted in support of treatment reimbursement currently lack metric-scale information. This complicates the process of deciding whether there is clear evidence of periodontitis. To address this difficulty, the evaluation systems of the present invention offer a statistical model that reliably associates estimated bone loss with the likelihood of periodontal disease being present. The input(s) to the statistical decision model call for the following annotations to be made on the appropriate radiographs:

mark as points, the location of the cemento-enamel junctions (CEJ) endpoints on each side of the tooth; and,
draw the line segment from each CEJ-endpoint location to the neighboring bone boundary that shows the maximum extent of the estimated bone loss.

Figure 8:
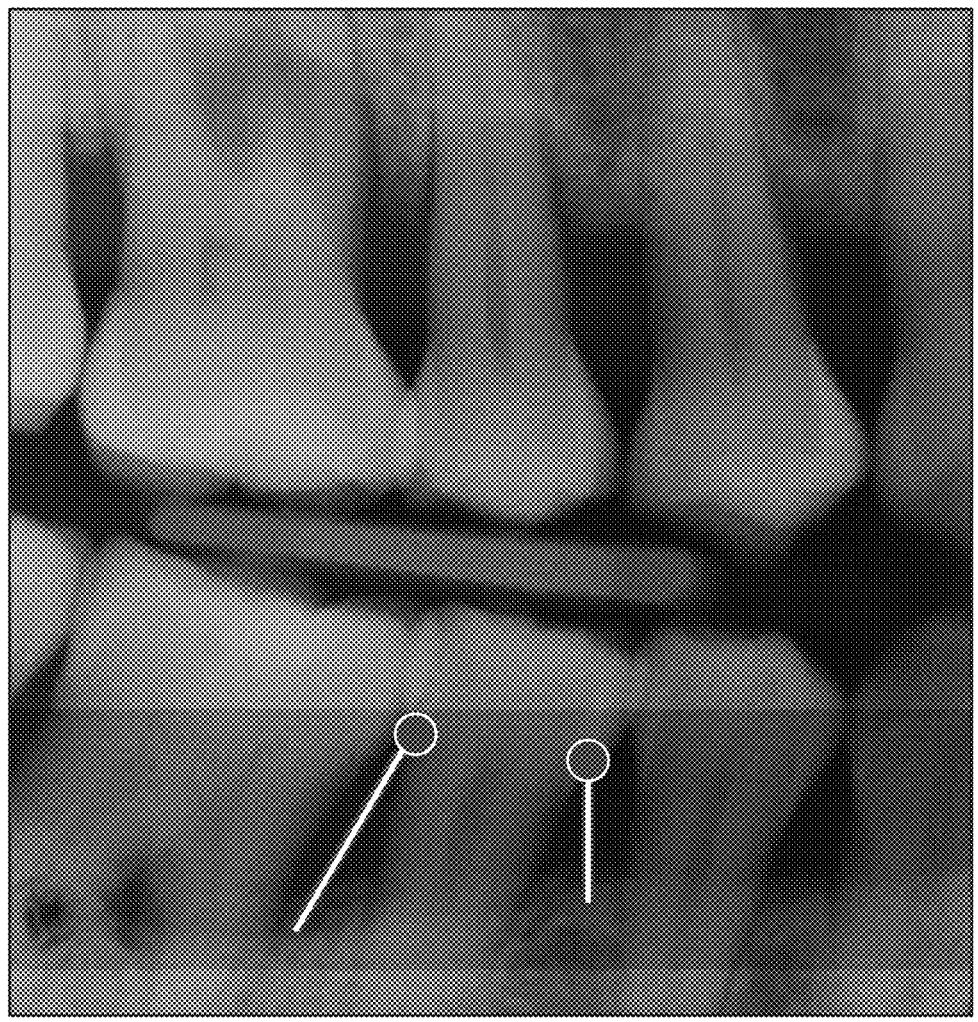
FIG. 8 illustrates marking a bone location and CEJ points on a digitized radiographic image in accordance with the principles of the present invention.

These annotations are illustrated in FIG. 8 where CEJ-endpoints are marked by dots. Bone loss estimates are indicated by line segment length.

When the annotation process is complete, the evaluation system records the geometric information in terms of each radiograph's pixel coordinate system and forwards the data to the bone loss decision-aid.

Step 4: Evaluate Decision-Aid Advisory Report. Using the radiograph annotation data acquired in Step 3 as input, the decision-aid produces a report indicating the probability that periodontitis is or is not present on the basis of the radiographic evidence. If metric-scale information were available in radiographs, estimating bone loss magnitude would be straight-forward, quite accurate and reproducible. However, given that scale information is not available, an alternative approach to expert opinion is desirable.

The evaluation system is such an alternative. It supplements expert interpretation of a claim's evidence with a software-based decision-aid developed through the application of pattern recognition methods to large quantities of dental radiographs in which evidence of periodontitis is and is not present. The result is a statistical model that correctly assesses radiographic data at the performance level of expert periodontal clinicians.

It is important to note that, insofar as the decision model is based on the analysis of much larger quantities of example data than individual examiners see, it usually outperforms individual experts and has been shown to perform reliably at or above the level of majority-voting committees of expert clinicians.

Step 5: Claim Examiner Evaluation and Report. The final adjudication of a periodontitis claim is the responsibility of the expert reviewer. While the advisory report of Step 4 is a key component of the total evidence evaluated by the claim examiner, it is not determinative by itself.

As described thus far, the systems of the present invention rely on human expert reviewers to manually annotate the radiographs on a display. Alternatively, the marking of the CEJ-endpoint locations and the placement of the bone-loss line-segment indicators may be carried out automatically through using digital image analysis implemented by the processor and thereby make the claim examination decision-aid entirely automatic.

The systems described herein will provide practical benefits to insurers and other users, potentially profoundly altering and improving their business processes related to periodontitis treatment insurance claims. Of particular importance among these possible practical benefits is the opportunity to have clinicians review only questionable claims, thereby increasing the volume of claims reviewed and improving clinician efficiency.

The purpose, benefits and application of the decision-aids of the present invention are outlined in Step 4 of Sections B and C above. In the following, the method by which the decision-aid's statistical model is constructed and applied is described as a three-stage process, consisting of (1) model construction, (2) model assessment and (3) model application.

Flowcharts and associated commentary for each of these stages appear below. The descriptions rely on the following specialized terminology, which is used to describe key landmarks in dental radiographs such as bitewings or periapical views. Where the term radiograph alone is used below, it refers specifically to either type of view.

Figure 9:
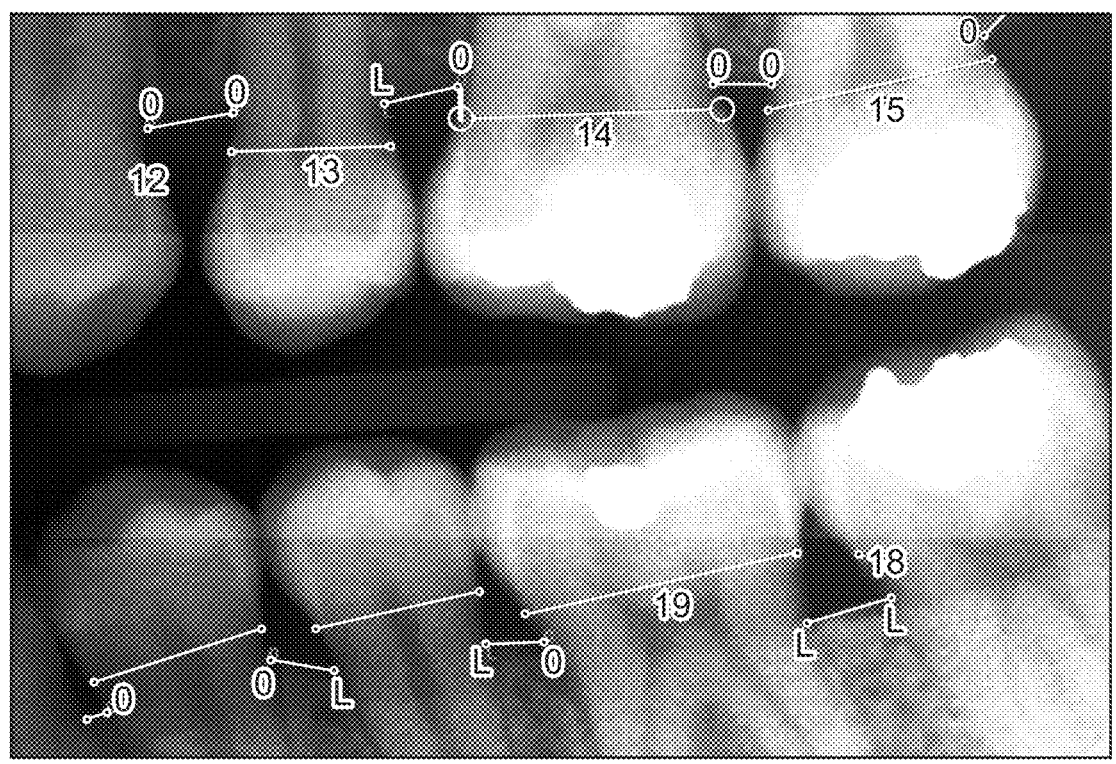
FIG. 9 illustrates quantitative measurements of bone depth and distance between CEJ points in accordance with the principles of the present invention.

CEJ-endpoint. The location of the cemento-enamel junction of a particular tooth may be seen on radiographs of fully-imaged normal teeth on a digital display where two CEJ-endpoints (left-side/right-side) may be identified. Example CEJ-endpoints are shown in FIG. 9, Tooth #14, at the sites marked by the centers of the circles.

CEJ-breadth. The length of the straight line-segment joining the CEJ-endpoints of a particular tooth. An example is shown in FIG. 9, Tooth #14, as the (red) line segment joining the centers of the red circles (i.e., CEJ-points).

Bone-boundary. The straight line-segment lying along the jaw bone crest between adjacent teeth.

Bone-separation. The length of the straight line segment joining a CEJ-endpoint to the same-side intersection of the bone-boundary with the tooth associated with the CEJ-endpoint.

Local ratio-feature. The numerical ratio, Bone-separation/CEJ-breadth, for a particular side of one tooth. For a given tooth, there may be one local ratio-feature only (left-side or right-side) or two local ratio-features (left-side and right-side, when both are present in the radiograph).

Global ratio-feature set. The set of all numerical ratios formed by dividing each Bone-separation by each CEJ-breadth evident in a given radiograph.

Evaluation Model Construction

Select Radiographic Data Type: Evaluation models are based on the use of either (1) bitewing radiographs, and/or (2) periapical radiographs. The model construction process is applicable to either type of radiograph or a combination of the two types.

Create Periodontitis Case Database: The patient case database used for model construction includes, at a minimum, the following anonymized data: (1) patient ID, (2) patient age, (3) patient gender, (4) bitewing and/or periapical radiographs. Additional data such as demographic and/or personal health information may be incorporated as well although that is not required to obtain satisfactory model accuracy in predicting the presence/absence of periodontitis.

All radiographic data is converted to a standard image format such as JPG, PNG, TIFF or BMP. The database is composed so as to include an approximately equal number of positive (periodontitis-present) and negative (periodontitis-absent) instances that amount to several thousand or more examples, on a per-tooth basis. The use of larger representative datasets for model construction is preferable since they normally lead to more accurate models.

Figure 10:
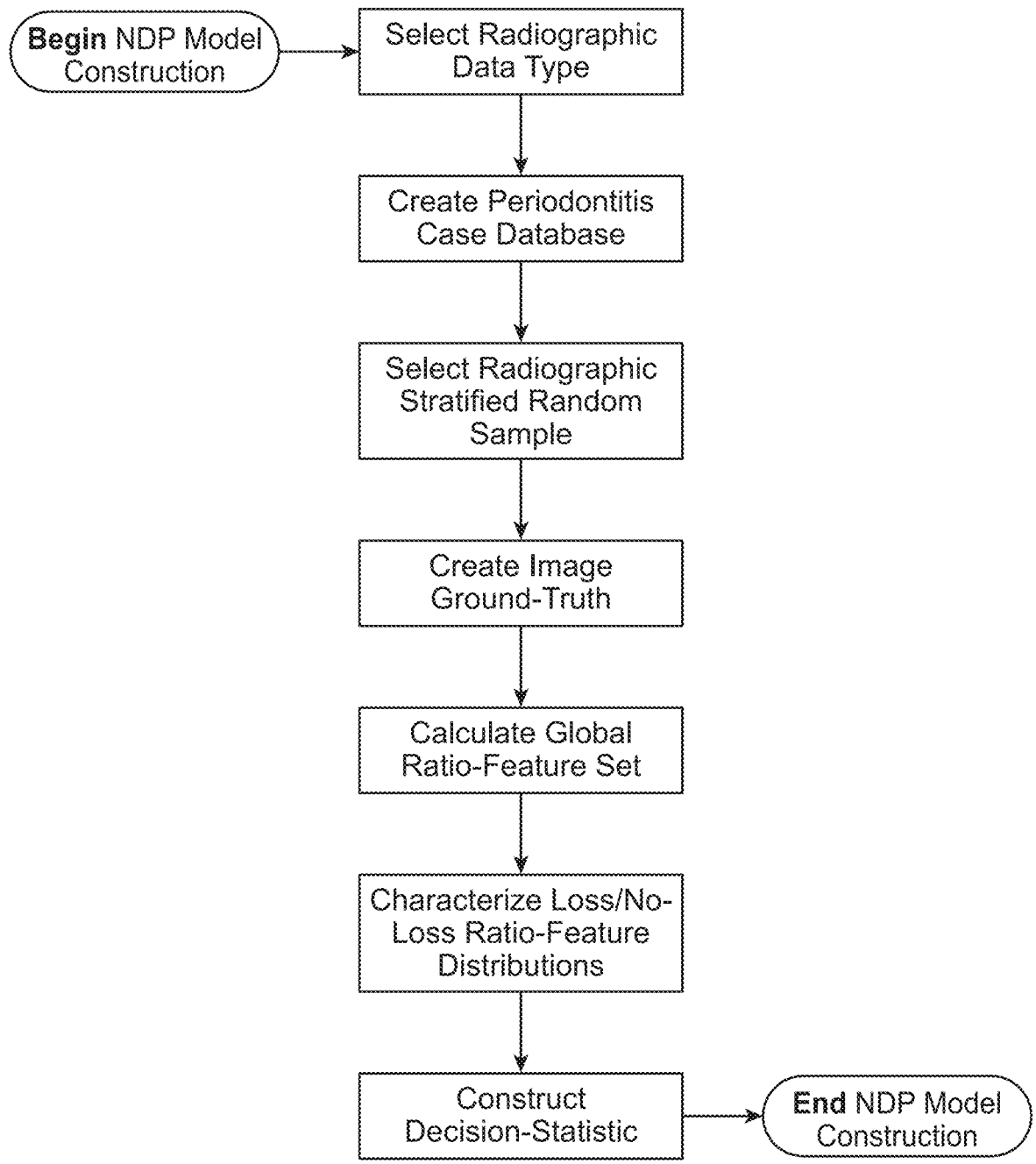
FIG. 10 is a chart illustrating the steps in creating a bone loss model in accordance with the principles of the present invention.

Select Radiographic Stratified Random Sample: The model construction process as shown in FIG. 10 relies upon the ability to separate the aggregate case database into three representative subsets, referred to as (1) training data, (2) stats data (used for model refinement), and (3) testing data. This is achieved through the use of stratified random sampling of the example data to ensure the three subsets are approximately equivalent with respect to the characterizing data (e.g., positive/negative cases, per-tooth basis; age; gender). In addition, the sampling is performed so as to ensure all data classes are approximately balanced in size for each of the training, stats and testing subsets.

Create Image Ground-Truth: The evaluation statistical model generalizes certain known characteristics of radiographs portraying significant bone loss (which is sufficient to suggest periodontitis is present) and also those radiographs not evidencing significant bone loss (and do not suggest the presence of periodontitis). These two cases are referred to in the following as the "loss" case and the "no-loss" case.

The categorization of the data into loss and no-loss cases on a per-tooth basis is provided in the form of image annotations by expert periodontal clinicians following visual review of each radiograph. Through this process, all CEJ locations evident in a radiograph are marked as CEJ-points and straight line segments designate bone-boundaries adjacent to the CEJ locations. Examples of such annotations are shown in FIG. 9 where the CEJ-points of a tooth are joined by a line segment marking the CEJ-breadth (i.e., the relevant width of the tooth) and the bone-boundaries are coded as "L" when bone loss is significant and "0" when it is not significant. The annotations are performed via a computer user interface that captures the relevant locations in terms of the radiograph's pixel coordinate system. Bone loss (if any) is measured as the bone-separation (defined above), recorded in terms of pixel units. The user interface automatically calculates bone-separation values for each viewable tooth-bone combination and enters the values in the appropriate image record. These values are then used to generate the local and global ratio-features.

Calculate Global Ratio-Feature Set: The global ratio-feature set is automatically calculated, using the ground-truth annotation data. In FIG. 9, the left-side local ratio-feature for Tooth #14 equals the left-side bone-separation (yellow line segment) divided by the CEJ-breadth of Tooth #14. The global ratio-feature for that bone-separation is calculated as the ratio of that bone-separation to all other CEJ-breadths available in the radiograph. Then, the full global ratio-feature set is determined by repeating the same calculations for each bone-separation available in the radiograph.

Characterize Loss/No-Loss Ratio-Feature Distributions: A loss ratio-feature distribution for a specific tooth is formed from the set of all global ratio-features gathered from all radiographs in the (representative) data set in which the ratio-features for the specific tooth exist.

A no-loss ratio-feature distribution is defined similarly. The loss and no-loss distributions corresponding to a specific tooth (e.g., Tooth #14) comprise the model for that individual tooth. In normal, healthy individuals there are therefore 32 unique models for each of the 32 teeth typically present.

Loss and no-loss distributions may or may not be normally distributed. In cases of sufficient data set sizes (e.g., over several thousand loss/no-loss instances, per-tooth), it is typical for the distributions to be normally distributed. In such cases, the distributions are fully-characterized by each distribution's mean and standard deviation. In the case of non-normal distributions, the distributions are summarized in the form of histograms and interpreted as probability density functions.

Construct Decision-Statistic: The decision statistic desired accepts as input, a tooth's identifier (e.g., #14) and a local ratio-feature, T, derived from a diagnostic radiograph and, as output, (1) identifies the more likely diagnostic case, no-loss or loss and (2) returns the relative likelihood that the tooth's condition is not (or is) evidence of periodontitis. Here, relative likelihood is taken to be the ratio of the probability density functions for the no-loss and loss cases at a specific value (T) of a ratio feature. It can be shown that this ratio is equivalent to calculating the ratio of the probabilities of the no-loss/loss cases for a particular ratio-feature value, say T.

Case A: Ratio-Feature Density Distributions are Normal

Figure 11:
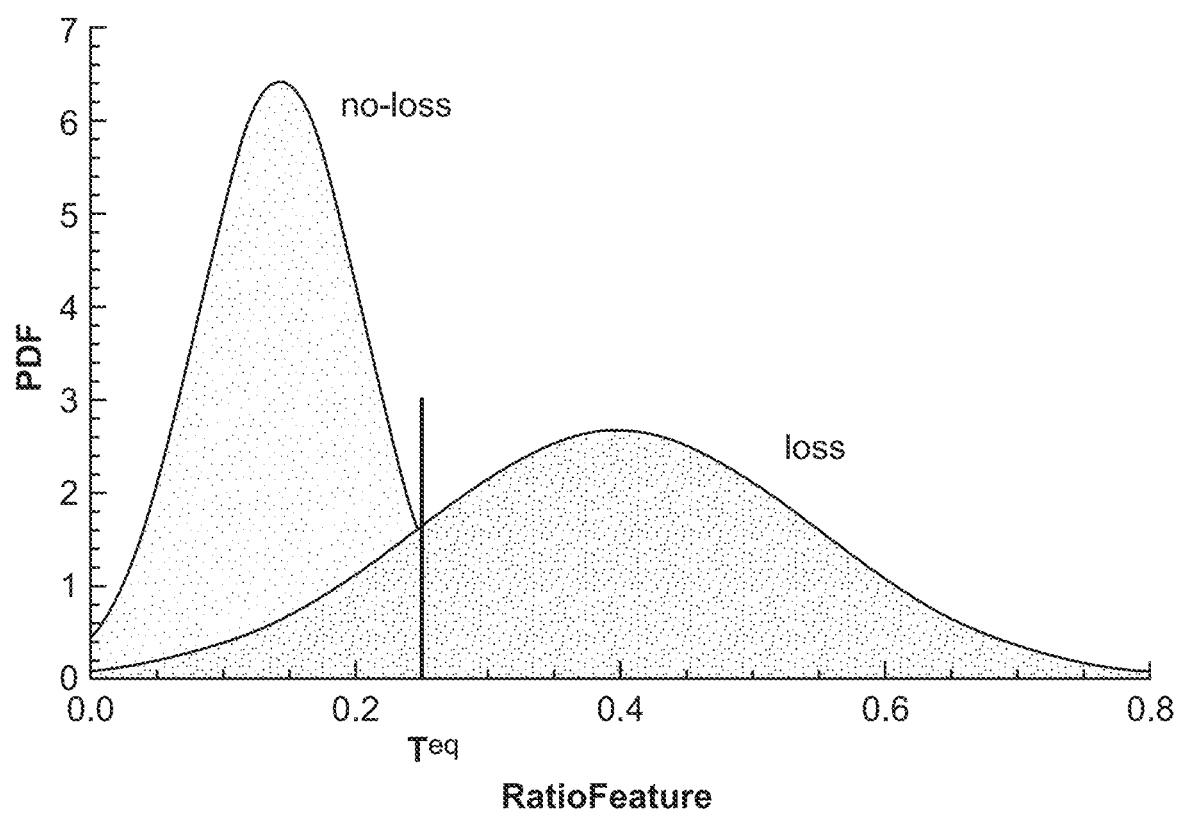
FIG. 11 is a graph illustrating use of a probability density distribution model for determining threshold bone loss for use in accordance with the principles of the present invention.

To illustrate the construction of the decision-statistic described in [0073], first assume the no-loss and loss distributions are normally distributed. Representative probability density distributions (PDF) distributions for Tooth #1 are shown in FIG. 11. The modeled no-loss PDF (yellow fill) peaks at its mean, 0.143, and has standard deviation 0.062 while the loss PDF (blue fill) has a mean of 0.398 and standard deviation of 0.150.

The red vertical line designates the larger ratio-feature value (of two possibilities) for which the two density functions are equal (about 0.25, in this example). Let us call $T^{eq}$ the (larger) ratio-feature value where the density functions assume the same value. Then it can be observed that ratio-feature values less than $T^{eq}$ correspond to no-loss cases because the no-loss density function value is greater than the loss density function value at the corresponding ratio-feature value. Similarly, ratio-feature values greater than $T^{eq}$ correspond to loss cases. The PDF distributions that arise in our periodontal modeling intersect at two ratio-feature values. We are always interested in only the intersection at the larger ratio-feature value.

Additionally, at a given ratio-feature value, it is meaningful to compare the density function values at that value, say T, by finding their ratio, $PDF_{no-loss}(T)/PDF_{loss}(T)$ because the ratio can be interpreted as the relative likelihood of the no-loss case over the loss case.

To make this clearer, consider the example distributions for Tooth #1 defined above. If T is 0.2, the no-loss/loss ratio of interest is PDF[NormalDistribution[0.143, 0.062], 0.2]/PDF[NormalDistribution[0.398, 0.150], 0.2]=4.22/1.11, or 3.8. So, if T=0.2, the no-loss case is 3.8 times more likely than the loss case.

In light of the forgoing, it can be seen that a straightforward decision rule concerning whether a radiograph provides evidence of periodontitis can be expressed in rule format. Namely, for a given tooth, if $T<T^{eq}$, then the evidence supports the no-loss case (i.e., no periodontitis), and, if $T>T^{eq}$, then the evidence supports the loss case (i.e., periodontitis present).

In practice, it may not be desirable to estimate $T^{eq}$ directly. In that case, an equivalent rule can be formulated in terms of the comparison of the modeled density function values for value T:

if $PDF_{no-loss}(T)/PDF_{loss}(T)>1$, then the evidence supports the no-loss case, and if $PDF_{no-loss}(T)/PDF_{loss}(T)<1$, then the evidence supports the loss case.

Case B. Ratio-Feature Probability Density Distributions are not Normal

In the event the modeled density functions do not correspond to normal distributions, the processes described above can be followed by working with histograms instead of analytic descriptions of the density functions.

In fact, parallel decision rules remain valid in this more general case, but $T^{eq}$ is replaced by a small interval, $T^{eq}\pm\delta$, around $T^{eq}$, where $\delta>0$; and, the ratio $PDF_{no-loss}(T)/PDF_{loss}(T)$ can again be interpreted as a relative likelihood. The size of that interval, $\delta$, is determined by the bin size of the histograms used to model the density functions. Larger bodies of training data can be expected to permit smaller bin sizes and, therefore, smaller values for $\delta$. It is desirable to use the smallest value of $\delta$ supported by the data available, since neither case (no-loss/loss) is favored for ratio-feature values in the interval $T^{eq}\pm\delta$.

Evaluation Model Assessment

Figure 12:
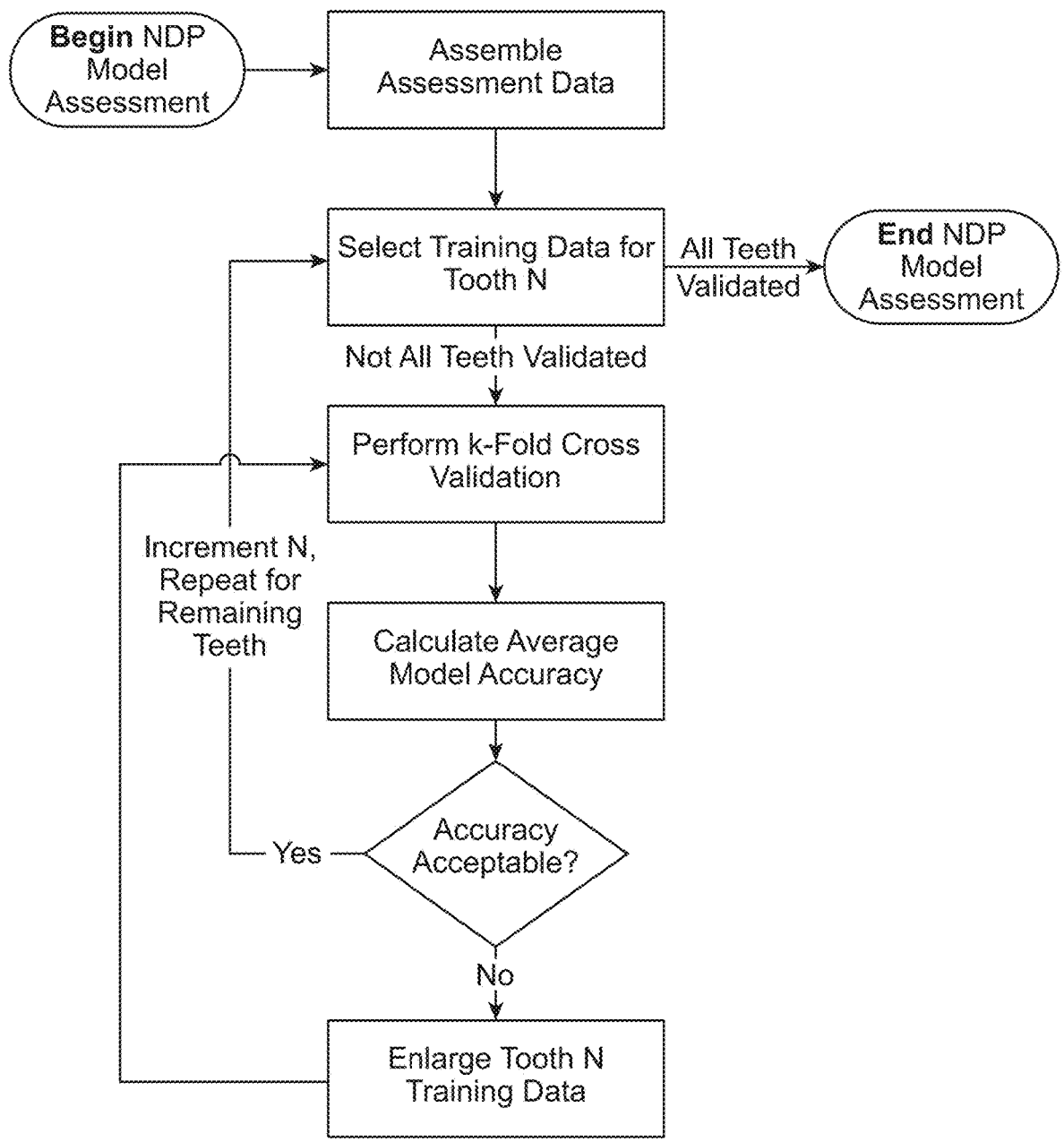
FIG. 12 is a logic flow chart showing assessment of the threshold bone loss model for use in accordance with the principles of the present invention.

Evaluation Model Assessment Flowchart: Referring to FIG. 12, the model construction process (Stage 1) can be expected to produce reliable predictive models for the interpretation of radiographs of dental patients that may have periodontitis. The model assessment process described here (Stage 2) is designed to determine whether the predictive no-loss/loss models constructed are likely to generalize to independent data sets and, therefore, be expected to perform well in practice.

Assemble Assessment Data: The model assessment data is the data set that results from merging the training, stats, and testing data created during the model construction process (see Stage 1, B.1-B.5 for details).

Each radiograph in this data set has been fully-annotated so that, for each tooth, CEJ-breadth and bone-separation are calculated and no-loss/loss ground-truth assigned where appropriate.

Select Training Data for Tooth N: Assume no-loss/loss models have been constructed for M different teeth, where M<32. Then, for Tooth N, with N=1, select all radiographs showing Tooth 1 and for which at least one local ratio-feature value is available.

Perform k-Fold Cross-Validation: For Tooth 1, k-fold cross-validation is performed with k=25. For k-fold cross-validation, the assessment data for Tooth N is randomly partitioned into k equal-sized subsamples. Then, in turn, for each subsample, a model is constructed using the k−1 subsamples for training and tested on the subsample not used in training. When k=25, this results in 25 accuracy tests based on 25 different constructed models. The method is effective, in part, because all data is used to train a model and all data is tested. Other values of k may be desirable in different application settings.

Calculate Average Model Accuracy: Each of the 25 k-fold tests gives rise to a 2-by-2 confusion matrix and accuracy is measured as the number of true positive and true negative decisions divided by the total number of positive (loss) and negative (no-loss) instances.

The average model accuracy is the average of the 25 individual tests.

Acceptable accuracy values are determined, ultimately, by the needs of specific applications.

Accuracy Acceptable: Periodontal no-loss/loss models accuracy rates between 85% and 90% are exemplary. These rates are competitive with those achieved by expert periodontal clinicians.

Therefore, for our purposes, average model accuracy ≥85% is acceptable. If the cross-validation process results in an average ≥85%, then the tooth number (N) is incremented and the validation process continues until all M models (M<32) have been validated.

Figure 13:
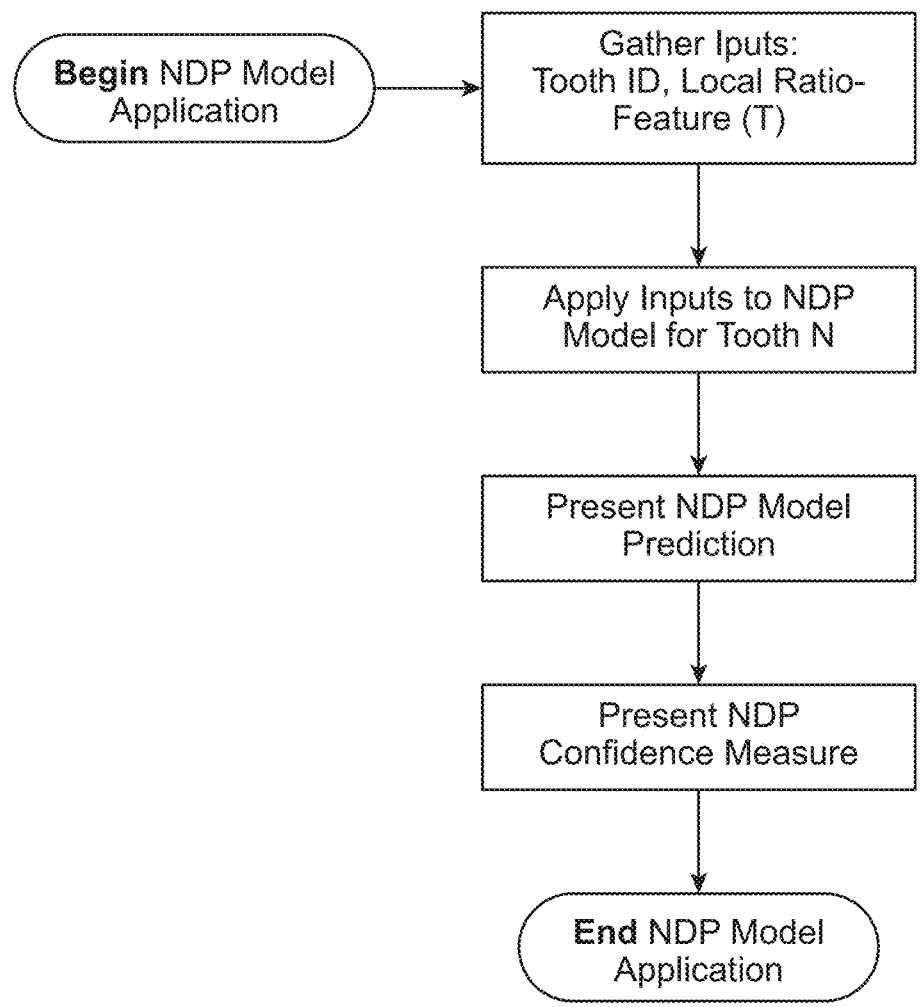
FIG. 13 is a logic flow chart showing application of the threshold bone loss model in accordance with the principles of the present invention.

Enlarge Tooth N Training Data: If the 25-fold cross-validation test results in accuracy less than 85%, then the assessment data set is enlarged with additional representative data, the Tooth N model is replaced by one based on the enlarged data set, and the cross-validation process repeated. Evaluation Model Application Flowchart (FIG. 13)

Gather Inputs: Tooth ID, Local Ratio-Feature (T): The evaluation decision-aid requires two input values: Tooth ID and one local ratio-feature (T).

Apply Inputs to Evaluation Model for Tooth N: The Tooth ID determines which tooth model to employ.

Present Evaluation Model Prediction: Then, for the identified tooth model, if $T<T^{eq}$, then the model predicts no-loss, signifying that the radiographic evidence does not support a diagnosis of periodontitis. Alternatively, if $T>T^{eq}$, then the model predicts loss, signifying that the radiographic evidence does support a diagnosis of periodontitis.

Present Evaluation Confidence Measure: The confidence measure, relative likelihood, is calculated as $PDF_{no-loss}(T)/PDF_{loss}(T)$. See above for details.

What is claimed is:

1. A method performed on a processor for screening a tooth for periodontal disease, said method comprising:
   providing a digitized radiographic image of a tooth having a tooth number according to a tooth classification system, wherein the image shows a bone boundary and a cemento-enamel junction (CEJ) of the tooth;
   loading the digitized radiographic image on the processor,
   marking the digitized radiographic image on the processor with a bone boundary location and a pair of CEJ points at opposite ends of the CEJ;
   calculating on the processor a ratio-value for the tooth between (a) a distance between the bone boundary location and the CEJ as numerator and (b) a distance between the CEJ points which represents a width of the tooth as denominator; and
   comparing the ratio-value for the tooth calculated on the processor with a database threshold ratio-value for a corresponding tooth from a database accessible by the processor, where a calculated ratio-value greater than the database threshold ratio-value is indicative of periodontal disease in the tooth.

2. A method as in claim 1, wherein locations on the bone boundary and pairs of CEJ points are selected to identify a maximum bone loss.

3. A method as in claim 1, wherein marking the digitized radiographic image comprises presenting the image on a monitor in communication with the processor and using an interface in communication with the processor to manually mark the bone boundary location and the pair of CEJ points.

4. A method as in claim 1, wherein marking the digitized radiographic image comprises automatically annotating the bone boundary location and the pair of CEJ points using an instruction set implemented by the processor.

5. A method as in claim 1, wherein the processor determines (a) a first distance between the bone boundary location and the pair of CEJ points and (b) a second distance between the CEJ points by counting pixels on the digitized image.

6. A method as in claim 1, wherein the radiographic image is one of a bitewing image, a periapical image, and a panoramic image.

7. A method as in claim 1, wherein providing the digitized radiographic image comprises digitizing a non-digital radiographic image.

8. A method as in claim 1, further comprising labeling digitized images with image identification information including image type and semantic content.

9. A method as in claim 1, further comprising digitizing non-digital patient records other than images to produce digitized patient records.

10. A method as in claim 9, further comprising labeling the digitized patient records with patient information.

11. A method as in claim 10, wherein the patient information comprises at least some of patient probe depth-charts, patient correspondence, and patient photographs.

12. A method as in claim 1, further comprising digitizing a non-digital radiographic image prior to providing the digitized radiographic image.

13. A method as in claim 1, wherein the database of threshold ratio-values has been generated by statistical analysis of the ratio between (a) a distance between the bone boundary location and the pair of CEJ points as numerator and (b) distances between CEJ-endpoints as denominator for a plurality of patients having pre-diagnosed tooth disease.

14. A method for screening periodontal insurance claims, said method comprising:
   receiving periodontal insurance claims identifying at least one tooth as having periodontal disease by tooth number according to a tooth classification system and including patient identification information and radiographic images of each tooth identified as having periodontal disease;
   screening each tooth identified as having periodontal disease by the steps of claim 1;
   forwarding those patient claims having at least one tooth identified as having periodontal disease with a calculated ratio-value less than the database threshold ratio-value to an expert for further evaluation when warranted by the probability of periodontal disease.

15. A method as in claim 14, wherein the radiographic images include bitewing, periapical, and/or panoramic images.

16. A method as in claim 14, wherein the patient identification information further comprises documents including photographs, probe depth-charts, correspondence, and/or claim forms.

17. A method as in claim 16, wherein all non-digital patient information is digitized and made part of a patient record forwarded to the expert.

18. A method as in claim 17, further comprising standardizing at least some of the patient identification information and radiographic images before forwarding a patient claim to the expert.

19. A processor configured to perform the following steps:
   receiving a digitized radiographic image of a tooth having a tooth number according to a tooth classification system, wherein the image shows a bone boundary and a cemento-enamel junction (CEJ) of the tooth;
   marking the digitized radiographic image with a bone boundary location and a pair of CEJ points at opposite ends of the CEJ;

calculating on the processor a ratio-value for the tooth between (a) a distance between the bone boundary location and the pair of CEJ points as numerator and (b) a distance between the CEJ-endpoints which represents a width of the tooth as denominator; and comparing the ratio-value for the tooth calculated on the processor with a database threshold ratio-value for a corresponding tooth from a database accessible by the processor, where a calculated ratio-value greater than the database threshold ratio value is indicative of periodontal disease in the tooth.

20. A processor as in claim 19, wherein locations on the bone boundary and pairs of CEJ points are selected to identify a maximum bone loss.

21. A processor as in claim 19, wherein marking the digitized radiographic image comprises presenting the image on a monitor in communication with the processor and using an interface in communication with the processor to manually mark the bone boundary location and the pair of CEJ points.

22. A processor as in claim 19, wherein marking the digitized radiographic image comprises automatically annotating the bone boundary location and the pair of CEJ points on the image using an instruction set implemented by the processor.

23. A processor as in claim 19, wherein the processor determines (a) a first distance between the bone boundary location and the pair of CEJ points and (b) a second distance between the CEJ points by counting pixels on the digitized image.

24. A processor as in claim 19, wherein the radiographic image is one of a bitewing image, a periapical image, and a panoramic image.

25. A processor as in claim 19, further comprising digitizing images where digitizing includes labeling each digitized image with image identification information including image type and semantic content.

26. A processor as in claim 25, wherein digitizing includes digitizing non-digital records other than images to produce digitized patient records.

27. A processor as in claim 26, wherein digitizing includes labeling at least some of the digitized patient records with patient information.

28. A processor as in claim 27, wherein the digitized patient records comprise at least some of patient probe depth-charts, patient correspondence, and patient photographs.

29. A processor as in claim 19, further comprising digitizing a non-digital radiographic image prior to providing the digitized radiographic image.

30. A processor as in claim 19, wherein a database of threshold ratio-values and corresponding decision probabilities (or confidence factors) has been generated by statistical analysis of the ratio between (a) a first distance between the bone boundary location and the pair of CEJ points as numerator and (b) a second distance between the pair of CEJ points as denominator for a plurality of patients having pre-diagnosed tooth disease.

* * * * *